United States Patent [19]

Uchihori et al.

[11] Patent Number: 4,945,048

[45] Date of Patent: Jul. 31, 1990

[54] PROCESS FOR PRODUCING L-SORBOSE BY SUBCULTURE OF SEED

[75] Inventors: Yuji Uchihori; Yasushi Sekitani; Ikuo Yoshida, all of Hikari, Japan

[73] Assignee: Takeda Chemical Industries, Ltd., Osaka, Japan

[21] Appl. No.: 197,404

[22] Filed: May 23, 1988

[30] Foreign Application Priority Data

May 23, 1987 [JP] Japan .................................. 62-126580

[51] Int. Cl.$^5$ ......................... C12P 19/02; C12R 1/01; C12R 1/02
[52] U.S. Cl. .................................... 435/105; 435/819; 435/822; 435/823
[58] Field of Search ................ 435/105, 819, 822, 823

[56] References Cited

PUBLICATIONS

Derwent Abstract 84-046821/08, Slave et al. (RO-73790)(Aug. 30, 1983).

*Primary Examiner*—Herbert J. Lilling
*Attorney, Agent, or Firm*—Wenderoth, Lind & Ponack

[57] ABSTRACT

A process for producing L-sorbose which comprises culturing a L-sorbose-producing bacterium to obtain a seed culture and subjecting the seed culture to a main fermentation with a batchwise fermentation procedure, wherein a part of said seed culture being subjected to subculture to prepare a seed culture for a next batch, while carrying out the main fermentation with the remainder of said seed culture, and this procedure being repeated, successively. An apparatus for this process is also disclosed.

4 Claims, 2 Drawing Sheets

PROCESS FOR PRODUCING L-SORBOSE BY SUBCULTURE OF SEED

FIELD OF THE INVENTION

The present invention relates to a process for producing L-sorbose and an apparatus therefor in which L-sorbose is produced from D-sorbitol by fermentation and a seed culture is subjected to subculture to promote growth of a L-sorbose-producing bacterium and to enhance its D-sorbitol-oxidizing activity.

BACKGROUND OF THE INVENTION

L-Sorbose is a useful substance as a raw material for synthesis of vitamin C (L-ascorbic acid) and, generally, it is produced by L-sorbose fermentation wherein D-sorbitol is oxidized by a L-sorbose-producing bacterium a representative example of which is one of bacteria of *Acetobacter, Gluconobacter suboxydans* (or *Acetobacter . suboxydans*).

Usually, for mass production, there is employed a so-called batchwise procedure wherein a main fermentor having a large volume is used. Although, recently, a continuous process has been studied, it can scarcely be employed for mass production because of instability of growth of the producing bacterium, contamination by other bacteria, remaining of unreacted sorbitol and the like. In such a batchwise fermentation procedure, for every batch, a seed culture is prepared from isolated pure bacterial cells of the producing bacterium by culturing them through several growth steps wherein a culture grown in a smaller culture tank is transferred in turn to a tank having a larger volume such as from a slant culture to a seed culture through a pre-culture and, finally, the seed culture thus obtained is used for a main fermentation to oxidize D-sorbitol to obtain L-sorbose.

In the above several growth steps, it is necessary to prevent contamination by other bacteria and to employ complicated operation for obtaining a pure culture and, further, much labor and many hours are required.

The present invention has been done in order to improve the above requirements in mass production of L-sorbose by a batchwise fermentation procedure such as complicated operation, much labor and many hours, and to carry out mass production of L-sorbose for a long period of time stably and economically. And, it has been completed based on the present inventors' finding that it is possible to subject a seed culture to subculture without lowering growth and oxidizing abilities of a L-sorbose-producing bacterium and thereby it is possible to eliminate the above preparation of a seed culture by several growth steps.

U.S. Pat. No. 4,156,630 discloses a process of fermentation wherein the microorganisms or enzymes are recycled into the fermentor after separating therefrom the fermentation filtrate and an apparatus therefor. However, it does not teach subculture of seed.

OBJECTS OF THE INVENTION

One object of the present invention is to provide a process for producing L-sorbose by subculture of seed.

Another object of the present invention is to provide an apparatus for carrying out the process of the present invention.

These objects as well as other objects and advantages of the present invention will become apparent to those skilled in the art from the following description by reference to the accompanying drawings.

SUMMARY OF THE INVENTION

Figure 1:
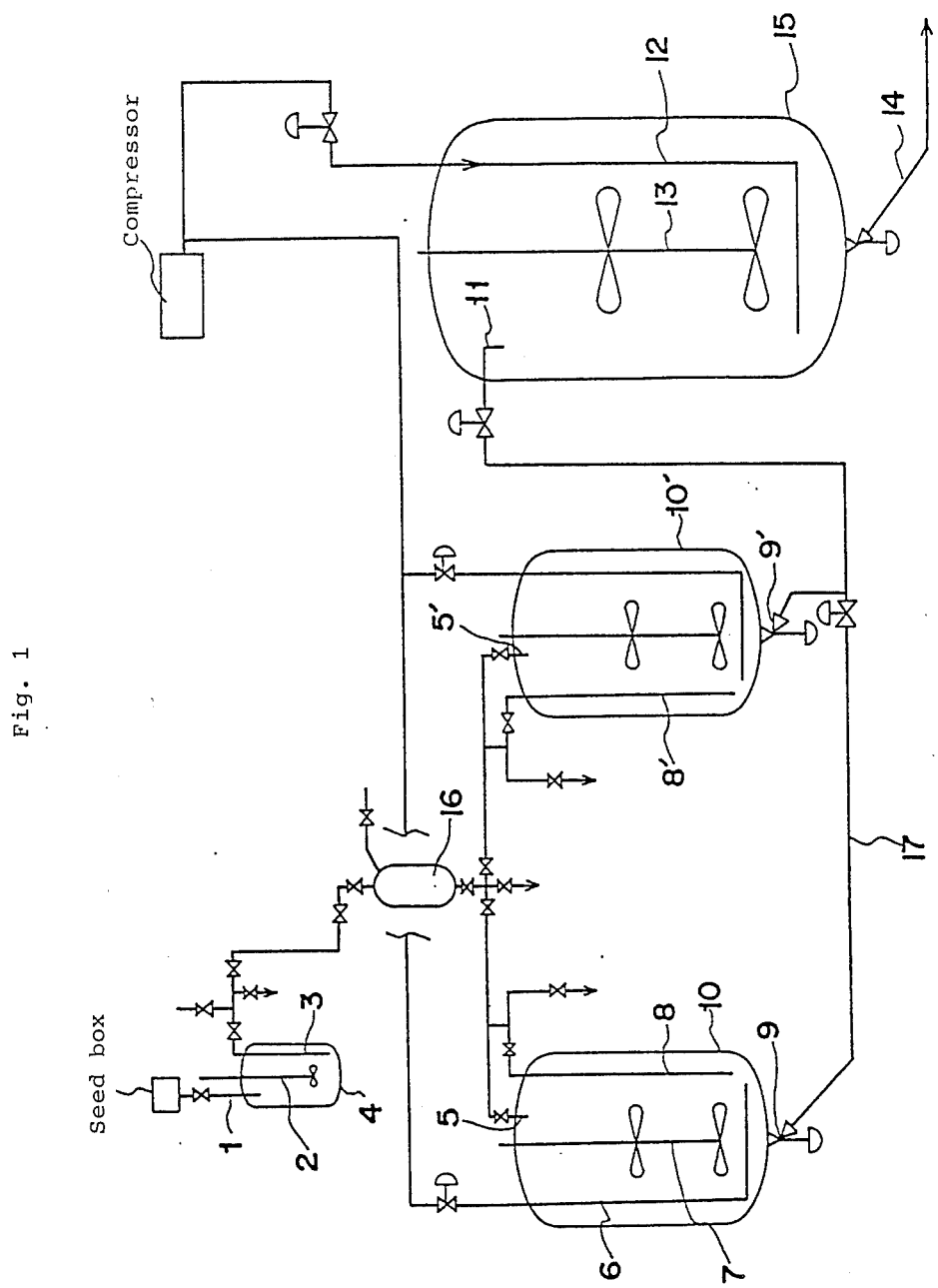
FIG. 1 is a general view illustrating one embodiment of the apparatus of the present invention.

In one aspect, the present invention provides a process for producing L-sorbose which comprises culturing a L-sorbose-producing bacterium to obtain a seed culture and subjecting the seed culture to a main fermentation with a batchwise fermentation procedure, wherein a part of said seed culture being subjected to subculture to prepare a seed culture for a next batch, while carrying out the main fermentation with the remainder of said seed culture, and this procedure being repeated, successively.

In another aspect, the present invention provides an apparatus for producing L-sorbose by subculture of seed which comprises a pre-culture tank, plural seed culture tanks and a main fermentor, each of said tanks being that for culturing aerobic microorganisms, said plural seed culture tanks being arranged in rows and each of them having means for transferring contents in at least one other seed culture tank thereto together with means for transferring contents in said pre-culture tank thereto, and said main fermentor having means for transferring contents in each seed culture tank thereto.

In still another aspect, the present invention provides an apparatus for producing L-sorbose by subculture of seed which comprises a pre-culture tank, a seed culture tank and a main fermentor, each of said tanks being that for culturing aerobic microorganisms, said seed culture tank having means for transferring a content in said pre-culture tank thereto, said pre-culture tank having means for returning a content in said seed culture tank thereto and said main fermentor having means for transferring a content in each seed culture tank thereto.

DETAILED DESCRIPTION OF THE INVENTION

The L-sorbose-producing bacterium used in the present invention is not specifically limited and there can be used any bacterium which is capable of oxidation of D-sorbitol to form L-sorbose. The representative examples thereof are microorganisms of the genus *Gluconobacter*, for example, seed strains of *Gluconobacter suboxydans* or *Gluconobacter oxydans*. As specific examples thereof, there are *Gluconobacter suboxydans* IFO 3254, IFO 3257, IFO 12528, IFO 3255, IFO 3256, IFO 3258 and IFO 3291 as well as *Gluconobacter oxydans* IFO 3189. These microorganisms are aerobes and gram-negative rods, and they have motility or non-motility and can grow under an acidic pH and produce ethanol from acetic acid.

In the process of the present invention, firstly, a L-sorbose-producing bacterium is adequately grown by a known method, for example, slant culture, pre-culture or the like to prepare seed for preparation of a 1st seed culture. Then, the seed thus obtained is transferred into a seed culture tank in which a previously sterilized medium for a seed culture has been placed to prepare the 1st seed culture.

This preparation of the seed culture can be carried out under aerobic conditions, for example, by bubbling air or oxygen into a liquid medium aseptically, at 26° to 35° C., preferably, 28° to 33° C. If necessary, according to a known method, pH can be adjusted to 4 to 7, dissolved oxygen can be adjusted to not less than 1 ppm, and it is possible to employ so-called sorbitol feeding culture wherein the bacterium is grown with addition of D-sorbitol to maintain its concentration in the medium of about 1 to 5%. The seed culture is grown until the producing bacterium is reached to its logarithmic growth phase or just before the end of the growth. Thereby, growth of the producing bacterium can be accelerated and its oxidizing ability can be enhanced. Usually, it takes about 20 to 24 hours until this state is obtained and preparation of the 1st seed culture is completed.

After completion of preparation of the 1st seed culture, a part of the culture is used as seed for preparation of a 2nd seed culture and the remainder is used for the main fermentation. The amount of the 1st seed culture to be used for preparation of the 2nd seed culture can be calculated from the growth rate of the producing bacterium and, particularly, it is preferable to choose the amount so that preparation of the 2nd seed culture takes the same period of time as that required for completion of the main fermentation with the remainder of the 1st seed culture, for example, about 20 to 24 hours.

According to the same manner as described with respect to preparation of the 1st seed culture, preparation of the 2nd seed culture is initiated at the same time of, and is advanced in parallel with the above main fermentation by using the above predetermined amount of the 1st seed culture in a seed culture tank.

On the other hand, the main fermentation can be carried out according to a known method. That is, the remainder of the 1st seed culture is transferred into a main fermentor wherein a liquid medium for the main fermentation has been placed and the concentration of the 1st seed culture in the main fermentation liquid is adjusted to, for example, 5 to 20% (v/v), preferably, 10 to 20% (v/v). Usually, the concentration of D-sorbitol in the main fermentation liquid is such that its total amount added becomes 10 to 50% (w/v). The fermentation is carried out under aerobic conditions, for example, by bubbling air or oxygen into the tank, at 26° to 35° C. and is completed by about 20 to 24 hours. After completion of the fermentation, contents of the main fermentor are discharged and, according to a conventional manner, L-sorbose is isolated and purified.

As described above, by adjusting the period of time required for the main fermentation so that it is the same as that required for preparation of the 2nd seed culture, the main fermentation is completed at the same time of completion of preparation of the 2nd seed culture. Then, according to the same manner as described with respect to the above 1st seed culture, a part of the 2nd seed culture is used as seed for preparation of a 3rd seed culture. And, the remainder is transferred to the main fermentor wherein a fresh medium for the main fermentation has been placed to carry out the main fermentation.

According to the present invention, by successively repeating the above cycle, the main fermentation can be continuously repeated with one batchwise main fermentor. Further, by the above subculture of the seed culture, growth and oxidizing abilities of the L-sorbose-producing bacterium can be maintained semipermanently without deterioration thereof. Furthermore, the above several growth steps of the producing bacterium for every batch which have been required for a conventional process can be eliminated.

The media for preparation of the seed culture and the main fermentation may be those conventionally used and, for example, there can be used media containing mainly D-sorbitol and optionally D-glucose, D-fructose, D-mannitol, molasses and the like as carbon sources; and inorganic nitrogen compounds such as ammonium sulfate, ammonium nitrate, ammonium acetate, ammonium chloride, ammonium phosphate and the like and organic nitrogen compounds such as amino acids, urea and the like as nitrogen sources. In addition, various metals, vitamins, nucleic acids, quinones and the like can be appropriately added.

The present invention also provides an apparatus for carrying out the above process for producing L-sorbose.

That is, the first aspect of the apparatus of the present invention comprises a pre-culture tank, plural, typically, two seed culture tanks and a main fermentor, each of said tanks being that for culturing aerobic microorganisms, said plural seed culture tanks being arranged in rows and each of them having means for transferring contents in at least one other seed culture tank thereto together with means for transferring contents in said pre-culture tank thereto, and said main fermentor having means for transferring contents in each seed culture tank thereto. Further, the second aspect of the apparatus of the present invention comprises a pre-culture tank, a seed culture tank and a main fermentor, each of said tanks being that for culturing aerobic microorganisms, said seed culture tank having means for transferring a content in said pre-culture tank thereto, said pre-culture tank having means for returning a content in said seed culture tank thereto and said main fermentor having means for transferring a content in each seed culture tank thereto.

Each of the pre-culture tank, the seed culture tank and the main fermentor used in the apparatus of the present invention may be a conventional one which is used for culturing aerobic microorganisms and there can be employed a tank which maintains aerobic conditions by known means such as a agitator or combination thereof with an air or oxygen introducing pipes and a venting pipe. Each tank can have openings and piping for feeding seed and medium and for discharging contents in the tank as usual. Depending upon a particular purpose, they are incorporated with valves, cocks, pumps and the like to constitute the means for transferring and returning contents in the present invention. Further, optionally, in the present invention, a weighing tank can be provided at an appropriate site such as between the pre-culture tank and the seed culture tank.

In order to carry out the process of the present invention by using the first aspect of the apparatus, for example, in the case that the apparatus has two seed culture tanks, firstly, the L-sorbose-producing bacterium adequately grown in the pre-culture tank is transferred from the pre-culture tank through the transferring means to the 1st seed culture tank in which a previously sterilized medium for the seed culture has been placed to carry out preparation of the 1st seed culture. When preparation is completed, a part thereof is transferred from the seed culture tank through the transferring means to the 2nd seed culture tank in which a previously sterilized medium for the seed culture has been placed. On the other hand, the liquid culture remained in the 1st seed culture tank is transferred to the main fermentor in which a medium for the main fermentation has been placed. Then, preparation of the 2nd seed culture in the 2nd seed culture tank is advanced in parallel with fermentation in the main fermentor. When preparation of the 2nd seed culture and the main fermentation is completed, contents in the main fermentor are discharged and transferred to isolation and purification steps of the desired L-sorbose. At the same time, according to the same manner as described above, a part of the 2nd seed culture is transferred to, now, the 1st seed culture tank and both preparation of the 3rd seed culture and the main fermentation with the remainder of the 2nd seed culture are carried out. By repeating this cycle successively, the fermentation in the main fermentor can be continuously repeated.

In order to carry out the process of the present invention by using the second aspect of the apparatus, firstly, the L-sorbose-producing bacterium adequately grown in the pre-culture tank is transferred from the pre-culture tank through the transferring means to the seed culture tank in which a previously sterilized medium for the seed culture has been placed to carry out preparation of the 1st seed culture. When preparation is completed, a part thereof is returned from the seed culture tank to the pre-culture tank to hold the culture therein. On the other hand, the liquid culture remained in the seed culture tank is transferred to the main fermentor in which a medium for the main fermentation has been placed. And, a medium for the seed culture is fed to the seed tank and the seed culture held in the pre-culture tank is transferred to the seed culture tank. Then, preparation of the 2nd seed culture in the seed culture tank is advanced in parallel with fermentation in the main fermentor. By repeating this cycle successively, the fermentation in the main fermentor can be continuously repeated. In the apparatus of the first aspect, the seed culture tank which is out of operation is present because preparation of the seed cultures is alternately carried out by using plural seed culture tanks. However, in the apparatus of the second aspect, this can be avoided.

Further, as described above, in the present invention, it is preferred to harmonize the amount and a period of time in preparation of the seed culture with those of the main fermentation. In this respect, it is preferred to choose volumes of the tanks in the apparatus of the present invention so as to meet this harmonization. For example, the volume ratio of the seed tank : the main fermentor is about 1:5 to 20.

EXAMPLE

The following Examples further illustrate the present invention in detail but are not to be construed to limit the scope thereof.

Firstly, the apparatus of the present invention is illustrated by reference to the attached drawings. In the attached drawings, FIG. 1 is a general view of one embodiment of the apparatus of the first aspect of the present invention which has two seed culture tanks.

The apparatus of this example has a pre-culture tank 4 having the seed feeding pipe 1, an agitator 2 and a liquid culture transferring and seed feeding pipe 3; a 1st seed culture tank having a seed feeding pipe 5, an air introducing pipe 6, an agitator 7 a liquid culture transferring pipe 8 and an opening 9 for discharging contents; a 2nd seed culture tank structure having a similar structure; and a main fermentor having a seed feeding pipe 11, an air introducing pipe 12, an agitator 13 and an opening 14 for discharging contents. A measuring tank 16 is provided between the pre-culture tank and the seed culture tanks 10 and 10'.

In order to produce L-sorbose by using this apparatus, the L-sorbose-producing bacterium adequately grown in the pre-culture tank 4 is transferred into the seed culture tank 10 by its transferring means, i.e., the seed feeding pipe 5 through the liquid culture transferring pipe 3 and the measuring tank 16. In the seed tank, a medium for the seed culture has been placed and preparation of the 1st seed culture is carried out with aeration and stirring by the air introducing pipe 6 and the agitator 7. When preparation is completed, a part of the 1st culture is transferred through the other transferring means, i.e., the liquid culture transferring pipe 8, the measuring tank 16 and the seed feeding pipe 5' into the 2nd seed culture tank 10' in which a medium for a seed culture has been placed. On the other hand, the liquid culture remained in the 1st seed culture tank 10 is transferred from the opening 9 for discharging contents through the line 17 and the transferring means, i.e, the seed feeding pipe 11 to the main fermentor 15 in which a medium for the fermentation has been placed. Then, preparation of the 2nd seed culture in the 2nd seed culture tank 10' is advanced in parallel with the main fermentation. When preparation of the 2nd seed culture and the main fermentation is completed, contents in the main fermentor 15 are discharged and transferred to isolation and purification steps of the desired L-sorbose. On the other hand, by reversing the above order, a part of the 2nd seed culture is transferred to the 1st seed culture tank 10 in which the medium for the seed culture has been placed, and the remainder of the 2nd seed culture is again transferred through the opening 9' and the seed feeding pipe 11 to the main fermentor 15 in which the medium for the main fermentation has been placed. By repeating this cycle successively, the seed culture tanks 10 and 10' are alternately used to carry out subculture of seed cultures and the fermentation in the main fermentor is continuously repeated without carrying out additional growth of the producing bacterium in the pre-culture tank 4.

Figure 2:
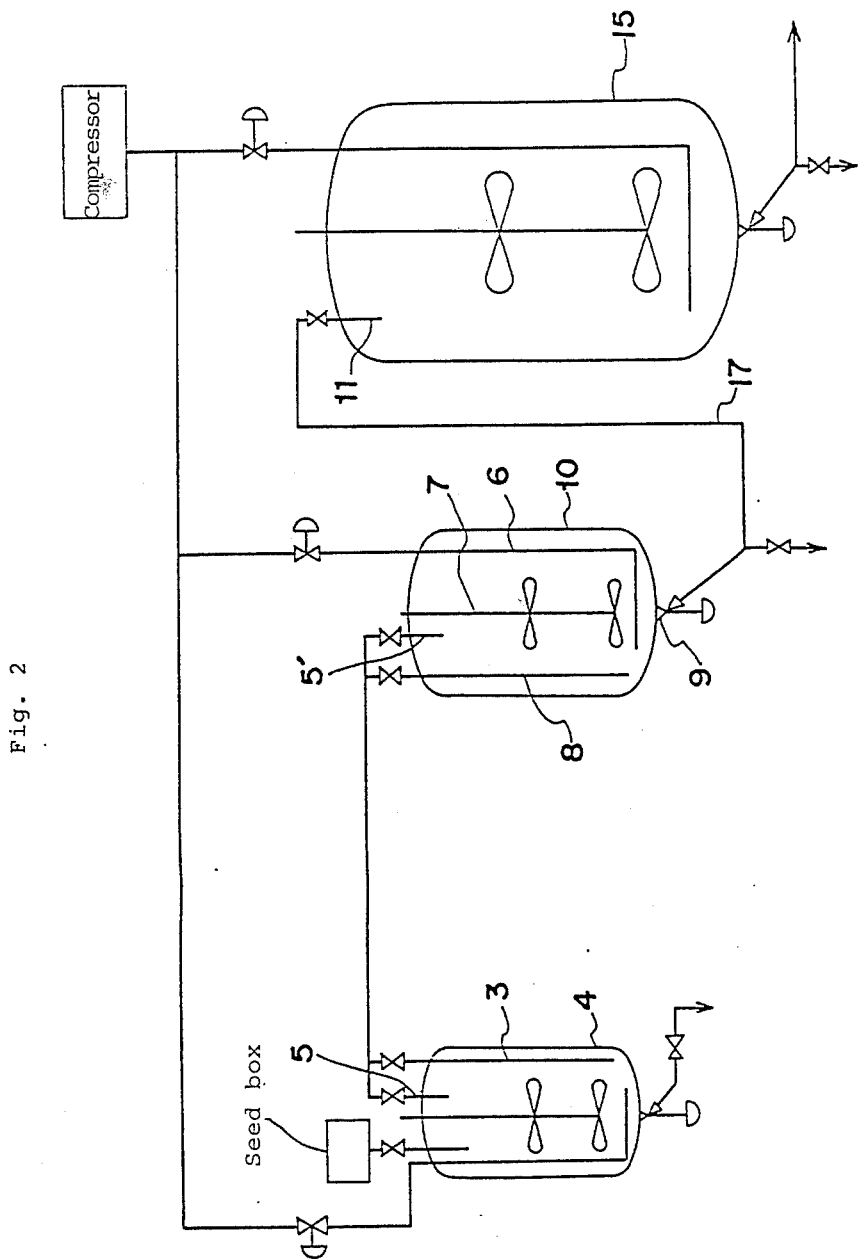
FIG. 2 is a general view illustrating another embodiment of the apparatus of the present invention.

The attached FIG. 2 is a general view of one embodiment of the second aspect of the apparatus of the present invention.

The apparatus of this example has a pre-culture tank 4, a seed culture tank 10 and a main tank 15 the structures of which are similar to those in FIG. 1.

In order to produce L-sorbose by using this apparatus, the L-sorbose-producing bacterium adequately grown in the pre-culture tank 4 is transferred to the seed culture tank 10 through the liquid culture transferring pipe 3 and the transferring means of the tank 10, i.e., the seed culture feeding pipe 5' . In the seed culture tank, a medium for the seed culture has been placed and preparation of the 1st seed culture is carried out with aeration and agitating by the air introducing pipe 6 and the stirrer 7. When preparation is completed, a part of the liquid seed culture is returned to the pre-culture tank 4 through the returning means, i.e., the liquid culture transferring pipe 8 and the seed feeding pipe 5 of the tank 4 to hold it therein. On the other hand, the liquid culture remained in the seed culture tank is transferred through the transferring means, i.e., the opening 9 for discharging, the line 17 and the seed feeding pipe 11 to a main fermentor in which a medium for the main fermentation has been placed. Further, a medium for the seed culture is again transferrd to the seed culture tank 10 and the 1st seed held in the pre-culture tank is transferred thereto. Then, preparation of the 2nd seed culture in the seed culture tank 10 is advanced in parallel with fermentation in the main fermentor 15. By repeating this cycle successively, the fermentation in the main fermentor can be continuously repeated.

The following Examples illustrate the process of the present invention.

EXAMPLE 1

25 ml Portions of a medium for a seed culture having the composition as shown in Table 1 were distributed in 250 ml-Erlenmeyer flasks and autoclaved at 120° C. for 15 minutes. A pre-culture (0.25 ml) of *Gluconobacter suboxydans* IFO 3254 was inoculated into the medium and cultured at 30° C. with stirring at 250 r.p.m. for 24 hours to obtain a 1st seed culture. As seed, 0.25 ml portion of the 1st seed culture was transferred into the second medium for the seed culture and subcultured under the same conditions as described with respect to the 1st seed culture.

TABLE 1

| Composition of medium | Concentration (w/v %) |
| --- | --- |
| D-Sorbitol | 20.00000 |
| Sodium glutamate | 0.20000 |
| Calcium carbonate | 0.01800 |
| Nicotinamide | 0.00300 |
| Calcium pantothenate | 0.00030 |
| Vitamin $B_2$ | 0.00010 |
| p-Aminobenzoate | 0.00010 |
| Monopotassium phosphate | 0.04700 |
| Yeast extract | 0.03000 |
| Magnesium sulfate | 0.01000 |
| Ferrous sulfate | 0.00015 |
| Manganese sulfate | 0.00001 |
| Anti-foaming agent | 0.00050 |

The remaining 1st seed culture (2.5 ml) was transferred into a main fermentation medium having the composition as shown in Table 2 (25 ml portions were distributed into 250 ml-Erlenmeyer flasks) and cultured at 33° C. with stirring at 250 r.p.m. for 20 hours.

TABLE 2

| Composition of medium | Concentration (w/v %) |
| --- | --- |
| D-Sorbitol | 31.00000 |
| Ammonium acetate | 0.03900 |
| Calcium carbonate | 0.01800 |
| Nicotinamide | 0.00300 |
| Calcium pantothenate | 0.00025 |
| Vitamin $B_2$ | 0.00010 |
| p-Aminobenzoate | 0.00001 |
| Monopotassium phosphate | 0.02000 |
| Magnesium sulfate | 0.01000 |
| Ferrous sulfate | 0.00015 |
| Manganese sulfate | 0.00001 |

Subculture of the seed culture was repeated 15 times and the seed culture resulted from each subculture was transferred into the main fermentation medium to carry out the main fermentation. Growth of the seed cultures by this subculture and the amount of sorbose produced in the main fermentation are shown in Table 3.

TABLE 3

| Number of subculture | Seed culture 24 hours Amount of cells* | Main fermentation 20 hours Amount of sorbose produced (%) |
| --- | --- | --- |
| 1 | 1950 | 29.80 |
| 2 | 1900 | 29.98 |
| 3 | 1900 | 30.52 |
| 4 | 1850 | 30.03 |
| 5 | 1925 | 29.86 |
| 6 | 1930 | 30.72 |
| 7 | 1900 | 30.46 |
| 8 | 1750 | 30.25 |
| 9 | 1800 | 29.74 |
| 10 | 1850 | 29.91 |
| 11 | 1725 | 30.16 |
| 12 | 1850 | 30.27 |
| 13 | 1850 | 29.43 |
| 14 | 1900 | 30.58 |
| 15 | 1825 | 30.23 |

*The amount of cells are corresponding to the value obtained by 5 times of the absorbance of the 1/5 diluted liquid culture determined at 660 nm.

EXAMPLE 2

By using three 5 liter-glass jar fermentors (hereinafter referred to as jar), they were arranged as seed culture tanks and a main fermentors as shown in FIG. 1. In two jars, a medium (2 liters) for a seed culture having the same composition as shown in Table 1 except that the concentration of sorbitol was 5% (w/v) was prepared by autoclaving at 120° C. for 15 minutes. A pre-culture (30 ml) of *Gluconobacter suboxydans* IFO 3254 was inoculated into one of these jars (1st seed culture tank) and culture was initiated under conditions of the temperature of 30° C., the aeration rate of 1500 ml/min. and the agitation rate of 700 to 800 rpm. Culture was continued for 24 hours with feeding a constant amount of sterilized sorbitol (so that the concentration thereof at the end of culture became 15%), since 5 hours past.

After culture was completed, the liquid seed culture (30 ml) was transferred to the other jar (2nd seed culture tank) as seed and subculture was carried out under the same conditions as described with respect to the 1st seed culture.

This was repeated successively and 10th seed subculture was prepared.

The above 1st seed culture (about 300 ml) obtained after 24 hours was transferred into the main fermentation medium (3 liters) having the same composition as shown in Table 2 and culture was continued at the temperature of 33° C. and the aeration rate of 3000 ml/min. for 20 hours.

Growth of the seed cultures by this subculture and the amount of sorbose produced in the main fermentation are shown in Table 4.

TABLE 4

| Number of subculture | Seed culture 24 hours Amount of cells* | Main fermentation 20 hours Amount of sorbose produced (%) |
| --- | --- | --- |
| 1 | 1975 | 29.85 |
| 2 | 2060 | 30.25 |
| 3 | 2040 | 29.97 |
| 4 | 2000 | 30.63 |
| 5 | 2025 | 30.63 |
| 6 | 1930 | 30.24 |
| 7 | 2040 | 30.36 |
| 8 | 2060 | 30.55 |
| 9 | 2150 | 30.41 |
| 10 | 2025 | 30.45 |

*The same as in Table 3.

EXAMPLE 3

A seed culture tank having the volume of 200 liters, a main fermentor having the volume of 2 m³ and a pre-culture tank were arranged as shown in FIG. 2. In the 200 liter-seed culture tank, a medium (100 liters) for a seed culture having the composition as shown in Table 1 was prepared by sterilizing at 110° C. for 30 minutes. A liquid pre-culture (about 1 liter) of *Gluconobacter suboxydans* IFO 3257 grown in the pre-culture tank was inoculated in the seed culture tank and culture was continued at the temperature of 30° C. and the aeration rate of 50 liter/min. for 24 hours. After culture was completed, a portion (1 liter) of the seed culture was placed in the pre-culture tank and the remainder thereof (about 100 liters) was transferred into a main fermentation medium (1 m³) having the same composition as shown in Table 2 and culture was continued at the temperature of 33° C. and the aeration rate of 500 liter/min. for 20 hours and the agitation rate of 210 to 230 rpm.

Immediately after transfer of the seed culture, another portion of the medium for the seed culture was prepared in the seed culture tank and the seed culture (1 liter) in the pre-culture tank was inoculated thereto. Then, culture was initiated under the same conditions as described above. After culture was completed, according to the same manner as described above, the resulting seed culture was transferred into the main fermentation medium and the main fermentation was carried out under the same conditions as described above. According to the same manner, subculture was repeated 21 times.

Growth of the seed cultures by this subculture and the amount of sorbose produced in the main fermentation are shown in Table 5.

TABLE 5

| Number of subculture | Seed culture 24 hours Amount of cells* | Main fermentation 20 hours Amount of sorbose produced (%) |
|---|---|---|
| 1 | 1600 | 30.16 |
| 2 | 1650 | 30.34 |
| 3 | 1900 | 30.50 |
| 4 | 1900 | 30.26 |
| 5 | 1900 | 30.74 |
| 6 | 1600 | 30.20 |
| 7 | 1900 | 30.30 |
| 8 | 1650 | 29.25 |
| 9 | 1650 | 30.55 |
| 10 | 1750 | 30.24 |
| 11 | 1800 | 29.58 |
| 12 | 1750 | 29.98 |
| 13 | 1725 | 30.06 |
| 14 | 1850 | 29.54 |
| 15 | 1700 | 29.92 |
| 16 | 1750 | 29.80 |
| 17 | 1900 | 29.60 |
| 18 | 1900 | 29.80 |
| 19 | 1900 | 29.36 |
| 20 | 2050 | 30.40 |
| 21 | 1950 | 30.14 |

*The same as in Table 3.

In the present invention, by subjecting a part of a seed culture to subculture for a next batch in a batchwise fermentation procedure of L-sorbose, growth and oxidizing abilities of a L-sorbose-producing bacterium can be maintained semipermanently without any deterioration thereof and preparation of seed for every batch which requires several steps can be eliminated. Further, by harmonizing the amount and the period of time for subculture of a seed culture with those of the main fermentation, subculture for the seed culture can be advanced in parallel with the main fermentation and the main fermentation can be continuously repeated with one main fermentor.

The reasons why subculture or continuous culture can not be employed in sorbose fermentation are lowering of oxidizing ability of a producing bacterium due to its mutation during culture for a long period of time, ineffective prevention of contamination by other bacteria from outside, and the like. However, according to subculture of a seed culture in the present invention, it is possible to carry out sorbose fermentation stably by a batchwise fermentation procedure.

What is claimed is:

1. A process for producing L-sorbose which comprises culturing a L-sorbose-producing bacterium of the genus gloconobacter to obtain a seed culture and subjecting the seed culture to a main fermentation with a batchwise fermentation procedure, wherein a part of said seed culture is subjected to subculture to prepare a seed culture for a next batch, while carrying out the main fermentation with the remainder of said seed culture, and this procedure being repeated, successively.

2. A process according to claim 1, wherein the amount and the period of time required for preparation of the seed culture for the next batch is harmonized with those of the main fermentation.

3. A process according to claim 2, wherein the period of time required for preparation of the seed culture for the next batch is 20 to 24 hours.

4. A process according to claim 1, wherein the L-sorbose-producing bacterium is *Gluconobacter suboxydans* or *Gluconobacter oxydans*.

* * * * *